US00PP09863P

United States Patent [19]

Hunter et al.

[11] Patent Number: Plant 9,863

[45] Date of Patent: Apr. 22, 1997

[54] 'HARROW SWEET' PEAR

[75] Inventors: David M. Hunter, Ontario; Frank Kappel, British Columbia; Richard E. C. Layne, Ontario; Harvey A. Quamme, British Columbia, all of Canada

[73] Assignee: Agriculture and Agri-Food Canada, Ontario, Canada

[21] Appl. No.: 542,398

[22] Filed: Oct. 12, 1995

[51] Int. Cl.[6] ..... A01H 5/00

[52] U.S. Cl. ..... Plt./36

[58] Field of Search ..... Plt./36

[56] References Cited

PUBLICATIONS

Swiss plant protection certificate No. 94.51.805, Harrow Sweet, Dec. 15, 1994.

Netherlands plant protection certificate No. 13270, Harrow Sweet, Sep. 7, 1993.

European Union plant protection certificate No. 93–51–956, Harrow Sweet, Nov. 23, 1994.

French plant protection certificate No. 6227, Harrow Sweet, Dec. 30, 1991.

"Harrow Sweet" Pear, Hunter, David M. et al, HortScience 27(12):1331–1334, 1992.

*Primary Examiner*—James R. Feyrer

*Attorney, Agent, or Firm*—Flynn, Thiel, Boutell & Tanis, P.C.

[57] ABSTRACT

A new and distinct cultivar of pear, which has been given the designation Harrow Sweet, bears a high quality late-season pear for the fresh market.

1 Drawing Sheet

FIELD OF THE INVENTION

The present invention relates to a pear cultivar and more specifically to a pear cultivar bearing a high-quality, late-season pear for the fresh market.

BACKGROUND OF THE INVENTION

Harrow Sweet is a fresh market pear which is distinguished in characteristics from the varieties similar to it, Bartlett, Harrow Delight and Harvest Queen. It is described by Hunter, D. M. et al, HortScience, vol. 27 (12):1331–1334, Dec. 1992, French Patent Breeders Rights No. D6277, issued November, 1991 and Swiss Plant Breeders Rights No. 94.51.805, issued 1994.

SUMMARY OF THE INVENTION

The new and distinct pear cultivar which has been given the designation of Harrow Street produces a high quality late-season pear for the fresh market.

DESCRIPTION OF THE INVENTION

Harrow Street originated from a cross of Bartlett×Purdue 80-51 made in 1965 by R. E. C. Layne. It was selected and asexually propagated by budding by H. A. Quamme, at Agriculture Canada Research Branch, Research Station, Harrow, Ont. N0R 1G0, Canada, and has been observed to remain true to the description set forth herein.

The tree is medium-sized, upright to spreading, and consistently very productive, even following exposure to winter minima of –28° C. There has been no evidence of biennial bearing. The bark of dormant shoots is reddish brown (R.H.S., 166-B) and shoot diameter is similar to that of Bartlett. The leaves are elliptic with acuminate tips. Leaf serrations are small but distinct. The flowers are white with pink to red anthers.

Figure 1:
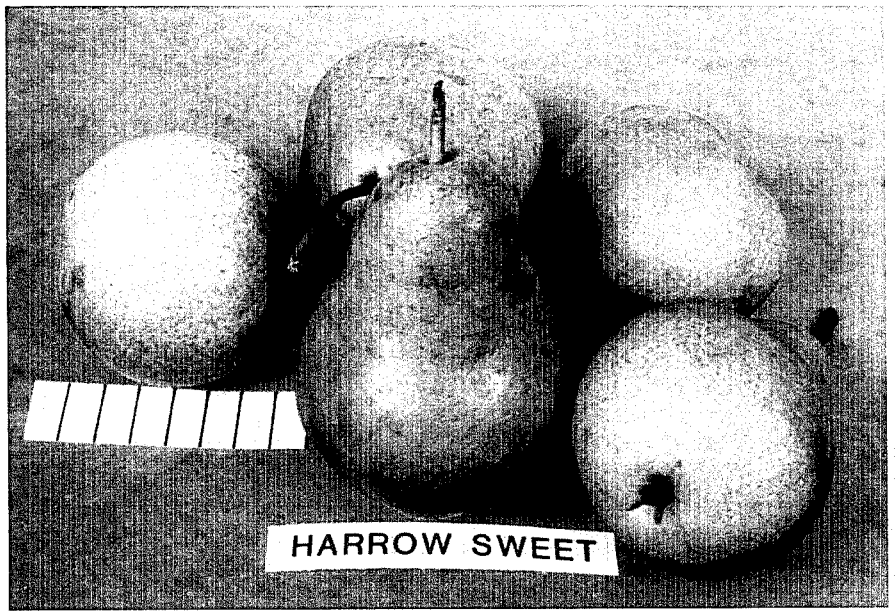
FIG. 1 is a photographic illustration of the whole fruit of Harrow Street pear.
Figure 2:
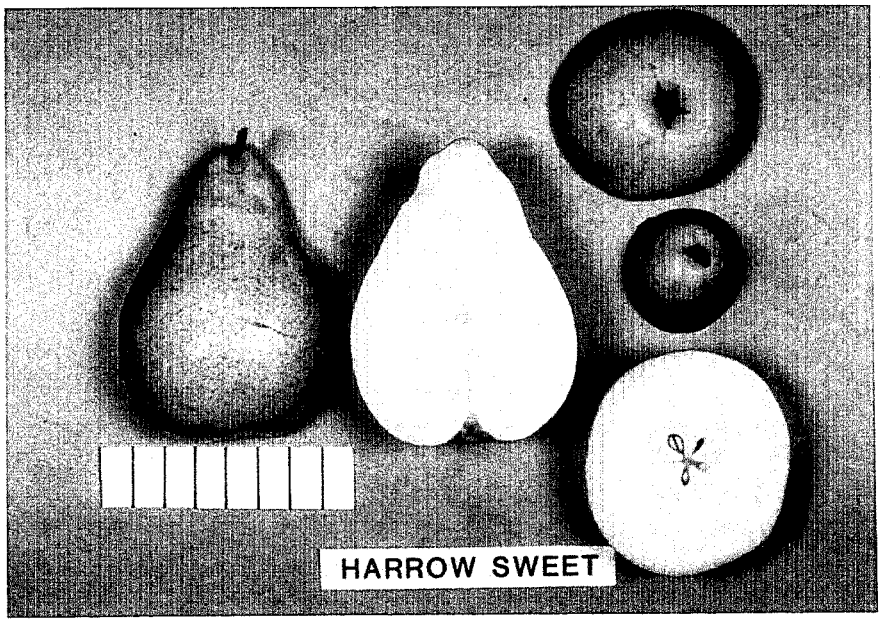
FIG. 2 is a photographic illustration of the sliced fruit of Harrow Sweet pear.

Harrow Sweet matured September 18 at Harrow, 23 days after Bartlett (Table 1). Preharvest fruit drop is not a problem. The medium to large fruit are slightly smaller than Bartlett on unthinned trees (Table 1). Fruit weight is improved by fruit thinning, since it is comparable to Bosc (Table 2). Fruit are pyriform in shape, with a shallow medium basin and an open calyx (FIG. 2). Fruit shape has been rated 5.2 using International Board for Plant Genetic Resources descriptors (Thibault et al., 1983); individual fruits have received ratings of 3.2, 3.4, 5.4 and 7.2. Following ripening at 20° C., the skin has an attractive, yellow ground color (color code 11A; Royal Horticultural Soc., 1966) with visible lenticels and a red blush where fully exposed to the sun. There may also be some russetting. The appearance of ripened fruit of Harrow Street has been rated slightly lower than Bartlett and Harrow Delight and equal to Harvest Queen (Table 1). However, in blind sensory evaluations using untrained or semitrained panelists, Harrow Sweet scored better in general appearance than Aurora, Bartlett, and Comice and equal to Conference (Table 3). The flesh is cream-white, very sweet, and juicy, with excellent flavor. Trained panelists have rated the flavor as good as that of Bartlett, but worse than Harrow Delight and Harvest Queen (Table 1). Using the Just Right scale (Robertson et al., 1990) the flavor was rated as slightly intense, texture was slightly soft, and the sweet source balance was considered just right (Table 3). The overall flavor rating of Harrow Sweet was similar to that of traditional high-quality cultivars (Table 3); it can be gritty around the core and the skin can be tough, but these do not detract from its overall quality. The fruit has been kept in cold storage (2° C.) at Harrow for about 10 weeks; longer-term storage (3 to 4 months) is possible at 0.5° C. (Masseron et al., 1991; Masseron and Trillot, 1991). If kept too long in storage, there can be some wilting at the stem end of the fruit.

TABLE 1

Fresh fruit performance of Harrow Sweet pear in comparison to Bartlett, Harrow Delight, and Harvest Queen at Harrow, Ont.

| Characteristic | Cultivar | | | |
|---|---|---|---|---|
| | Bartlett | Harrow Delight | Harvest Queen | Harrow Sweet |
| Years evaluated | 17 | 18 | 19 | 16 |
| Harvest dates | | | | |
| Avg. | 26 Aug. | 11 Aug. | 18 Aug. | 18 Sept. |
| Earliest | 16 Aug. | 5 Aug. | 6 Aug. | 30 Aug. |
| Latest | 9 Sept. | 16 Aug. | 31 Aug. | 8 Oct. |
| Size (mm)[z] | | | | |
| Length | 82 ± 1[y] | 80 ± 1 | 73 ± 1 | 84 ± 2 |
| Diam | 64 ± 1 | 59 ± 1 | 58 ± 1 | 62 ± 1 |
| Ratings | | | | |
| Appearance[x] | 8.0 ± 0.1 | 7.9 ± 0.2 | 7.4 ± 0.2 | 7.4 ± 0.2 |
| Flavor[x] | 8.0 ± 0.2 | 8.2 ± 0.1 | 8.2 ± 0.1 | 7.8 ± 0.2 |
| Texture[x] | 7.8 ± 0.1 | 7.9 ± 0.2 | 8.5 ± 0.2 | 6.8 ± 0.1 |
| Grit[w] | 3.8 ± 0.1 | 3.9 ± 0.1 | 4.5 ± 0.1 | 3.2 ± 0.1 |
| Juiciness[v] | 3.9 ± 0.1 | 4.4 ± 0.1 | 4.2 ± 0.1 | 4.3 ± 0.1 |
| Core size[u] | 3.1 ± 0.1 | 3.1 ± 0.1 | 2.4 ± 0.1 | 3.8 ± 0.2 |
| Weighted score[t] | 79.6 ± 1.1 | 80.7 ± 1.2 | 80.6 ± 1.3 | 75.2 ± 1.7 |

[z]Fruit produced from unthinned trees. A random sample of two to three fruit per year was measured.
[y]Mean ± SE.
[x]Appearance, flavor, and texture ratings are on a 1 (poor) to 10 (excellent) scale, as determined by trained panelists.
[w]Grit is on a 1 (undesirable, i.e., large and/or many grit cells) to 5 (desirable, i.e., very small and/or few or no grit cells) scale.
[v]Juiciness is on a 1 (dry) to 5 (very juicy) scale.
[u]Core size is on a 1 (small) to 5 (large) scale.
[t]Weighted score = (3 × appearance) ± (5 × flavor) + (2 × texture).

TABLE 2

Mean fruit weight of Anjou, Bosc, and Harrow Sweet pear grown at Summerland, B.C.[z]

| Cultivar | 1989 | 1990 | 1991 |
|---|---|---|---|
| | g/fruit | | |
| Anjou | 211 ± 9 a[y] | 158 ± 10 b | 147 ± 9 b |
| Bosc | 180 ± 15 ab | 202 ± 19 a | 181 ± 2 a |
| Harrow Sweet | 148 ± 16 b | 137 ± 6 b | 190 ± 6 a |

[z]Data were collected from five single-tree replicates planted in Spring 1987. In 1991, fruit were hand-thinned to 15 to 20 cm apart following June drop. No hand-thinning was conducted in 1989 or 1990.
[y]Mean ± SE. Mean separation within columns by Waller-Duncan k ratio test, P = 0.05, k = 100.

TABLE 3

Perception of pear fruit quality by untrained[z] and semitrained[y] panelists at Summerland, B.C.

| Cultivar | General appearance[x] | Flavor[w] | Texture[w] | Sour/Sweet balance[w] | Overall flavor rating[x] |
|---|---|---|---|---|---|
| Aurora | 2.4 ± 0.3b[v] | −0.1 ± 0.3a | −0.7 ± 0.3c | 0.0 ± 0.2ab | 1.9 ± 0.4b |
| Bartlett | 2.6 ± 0.2b | −0.6 ± 0.5a | −0.8 ± 0.3c | −0.8 ± 0.2b | 3.0 ± 0.3a |
| Comice | 3.3 ± 0.4a | −0.3 ± 0.4a | 0.1 ± 0.3ab | 0.0 ± 0.3ab | 3.2 ± 0.4a |
| Conference | 1.6 ± 0.2c | −0.6 ± 0.3a | 0.6 ± 0.2a | 0.3 ± 0.2a | 2.9 ± 0.3a |
| Harrow Sweet | 1.3 ± 0.2c | 0.4 ± 0.2a | −0.3 ± 0.3bc | 0.0 ± 0.3ab | 2.4 ± 0.4ab |

[z]Judges were not familiar with rating scales or procedures used. Nine judges were used to determine general appearance, flavor, texture, and sour/sweet balance.
[y]Judges were familiar with rating scale used. Twelve judges were used to determine overall flavor, and tasting was done in individual booths.
[x]Scale for general appearance and overall flavor rating is a five-point hedonic scale where 1 = like very much and 5 = dislike very much.
[w]Just Right scale was used for flavor (−2 = much too bland and 2 = much too intense), texture (−2 = much too soft and 2 = much too hard) and sour/sweet balance (−2 = much too sour and 2 = much too sweet). A rating of 0.1 is considered Just Right (Robertson et al., 1990).
[v]Mean ± SE. Mean separation within columns by Waller-Duncan k ratio test, p = 0.05, k − 100.

When ripened fruit are processed as halves or puree, Harrow Sweet does not rate as highly as Bartlett and generally is rated equal to or lower than Harrow Delight and Harvest Queen. While acceptability of processed fruit products is good, the quality is probably not sufficiently high for Harrow Sweet to have potential as a processed pear in the present market.

Harrow Sweet has excellent resistance to fire blight. Using natural fire blight infection scores (van der Zwet et al., 1970), resistance of Harrow Sweet is between that of Harvest Queen and Harrow Delight, while the response to artificial inoculation is similar to that of Harrow Delight. Fire-blight resistance of Harrow Sweet is much greater than that of Bartlett, Bosc, or Anjou. Based on field observations, Harrow Sweet appears to be less susceptible to pear psylla (*Cacopsylla pyricola* Foerster) than other cultivars, especially Harrow Delight.

Harrow Sweet is reciprocally pollen-compatible with Bartlett. It will also pollinate Harrow Delight and, to a lesser extent, Harvest Queen. Harrow Sweet blooms slightly ahead of Bartlett; at Harrow, first bloom is 1 day before Bartlett, while information from France indicates bloom is 2 to 4 days earlier than Bartlett (Masseron et al., 1991).

In Ontario, Harrow Sweet has been compatible with *P. communis* rootstocks, such as Bartlett seedling and Old Home×Farmingdale (OHF) clones 69 and 87. Harrow Sweet is also compatible for direct grafting onto quince (Cydonia clones BA29 and EMC) and OHF clone 333 (Brokmal; Masseron et al., 1991).

Because of its resistance to fire blight, Harrow Sweet has performed better than Bartlett in a replicated trial planted at Harrow in 1984 (Table 4). Fire blight has resulted in the loss of 50% of the Bartlett trees, and surviving trees of Bartlett are also affected by fire blight. Harrow Sweet is more precocious than Bartlett, producing fruit from lateral buds on first-year wood and on spurs, thus coming into production in the 2nd or 3rd year after planting. In Summerland, Harrow Street produced significantly higher yields in the 2nd and 3rd years after planting than Anjou or Bosc. By the 5th year after planting, annual and cumulative yields of Harrow Sweet were higher, but not significantly so, than those of Bosc and Anjou (Table 4). Harrow Sweet appears to be adapted to regions where Bartlett and Bosc have been successfully grown and can be considered a replacement for Bosc in areas where fire blight has presented serious problems.

TABLE 4

Annual and cumulative yields of Harrow Sweet pear and standard cultivars grown at Harrow, Ont.,[z] and Summerland, B.C.[y]

| | Harrow (kg/tree) | | Summerland (kg/tree) | | |
|---|---|---|---|---|---|
| Year | Bartlett[x] | Harrow Sweet | Anjou | Bosc | Harrow Sweet |
| 1986 | 0.0 b[w] | 2.0 ± 0.0 a[v] | | | |
| 1987 | 0.2 ± 0.0 b | 5.7 ± 1.5 a | | | |
| 1988 | 3.8 ± 1.4 a | 4.6 ± 1.0 a | 0.0 b | 0.1 ± 0.1 b | 2.5 ± 0.3 a |
| 1989 | 5.6 ± 1.4 b | 13.3 ± 2.2 a | 1.2 ± 0.3 b | 3.2 ± 0.8 b | 7.7 ± 1.4 a |
| 1990 | 0.4 ± 0.1 b | 17.5 ± 3.5 a | 2.4 ± 0.7 a | 4.5 ± 1.2 a | 8.1 ± 2.7 a |

TABLE 4-continued

Annual and cumulative yields of Harrow Sweet pear and standard cultivars grown at Harrow, Ont.,[z] and Summerland, B.C.[y]

| | Harrow (kg/tree) | | Summerland (kg/tree) | | |
|---|---|---|---|---|---|
| Year | Bartlett[x] | Harrow Sweet | Anjou | Bosc | Harrow Sweet |
| 1991 | 4.3 ± 0.3 a | 8.8 ± 1.8 a | 9.4 ± 1.4 a | 16.5 ± 4.6 a | 16.4 ± 4.9 a |
| Cumulative yield to 1991 | 14.3 ± 2.4 b | 51.9 ± 9.2 a | 12.9 ± 2.0 a | 24.3 ± 5.7 a | 34.7 ± 9.0 a |
| TCSA[u] ($cm^2$) | 42.9 ± 6.8 b | 68.1 ± 13.8 a | 18.3 ± 1.7 a | 16.6 ± 2.8 a | 17.2 ± 3.6 a |
| Yield efficiency[t] | 0.35 ± 0.11 b | 0.80 ± 0.15 a | 0.70 ± 0.08 b | 1.41 ± 0.18 a | 1.92 ± 0.20 a |

[z]Data collected from four single-tree replicates planted in 1984, first cropped in 1986.
[y]Data collected from five single-tree replicates planted in 1987, first cropped in 1988.
[x]For Bartlett, n = 2. Two of four trees were lost to fire blight; surviving two trees are also affected.
[w]Mean separation within locations and years by Waller-Duncan k ratio test, P = 0.05, k = 100.
[v]Mean ± SE.
[u]TCSA = trunk cross-sectional area ($cm^2$) measured in Fall 1991 at Harrow and in Spring 1991 at Summerland.
[t]Yield efficiency = cumulative yield to 1991/$cm^2$ TCSA.

What is claimed is:

1. A new and distinct pear tree substantially as shown and described herein.

* * * * *

UNITED STATES PATENT AND TRADEMARK OFFICE

CERTIFICATE OF CORRECTION

PATENT NO. : PP09863

DATED : April 22, 1997

INVENTOR(S) : David M. HUNTER

It is certified that error appears in the above-indentified patent and that said Letters Patent is hereby corrected as shown below:

Column 1, line 26; change "Street" to ---Sweet---.

Column 1, line 32; change "Street" to ---Sweet---.

Column 2, line 5; change "(R.H.S., 166-B)" to ---(RHS, 166-B)---.

Column 2, line 34; change "sweet source" to ---sweet sour---.

Column 4, line 27; change "p=0.05" to ---P=0.05---.

Column 4, line 49; change "whle" to ---while---.

Column 5, line 6; change "Street" to ---Sweet---.

Signed and Sealed this

Twenty-third Day of December, 1997

Bruce Lehman

*Attest:*

BRUCE LEHMAN

*Attesting Officer*

*Commissioner of Patents and Trademarks*